(12) United States Patent
Harris

(10) Patent No.: US 10,881,542 B2
(45) Date of Patent: Jan. 5, 2021

(54) STENT DELIVERY DEVICE

(71) Applicant: BOSTON SCIENTIFIC SCIMED, INC., Maple Grove, MN (US)

(72) Inventor: Colby Harris, Weston, MA (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 248 days.

(21) Appl. No.: 15/474,359

(22) Filed: Mar. 30, 2017

(65) Prior Publication Data
US 2017/0281381 A1 Oct. 5, 2017

Related U.S. Application Data

(60) Provisional application No. 62/318,283, filed on Apr. 5, 2016.

(51) Int. Cl.
*A61F 2/95* (2013.01)
*A61F 2/966* (2013.01)
*A61F 2/04* (2013.01)
*A61F 2/82* (2013.01)
*A61M 25/00* (2006.01)

(52) U.S. Cl.
CPC .............. *A61F 2/966* (2013.01); *A61F 2/04* (2013.01); *A61F 2/82* (2013.01); *A61F 2/9517* (2020.05); *A61F 2002/044* (2013.01); *A61F 2002/9528* (2013.01); *A61F 2002/9534* (2013.01); *A61F 2002/9665* (2013.01); *A61M 25/0068* (2013.01)

(58) Field of Classification Search
CPC ...... A61F 2002/9665; A61F 2002/9517; A61F 2002/044; A61F 2002/9528; A61F 2002/9534; A61F 2/04; A61F 2/966; A61F 2/82; A61M 25/0068
See application file for complete search history.

(56) References Cited

U.S. PATENT DOCUMENTS

| | | |
|---|---|---|
| 4,990,151 A | 2/1991 | Wallsten |
| 5,026,377 A | 6/1991 | Burton et al. |
| 5,366,504 A | 11/1994 | Andersen et al. |

(Continued)

FOREIGN PATENT DOCUMENTS

| | | |
|---|---|---|
| EP | 0775470 A1 | 5/1997 |
| FR | 2939637 A1 | 6/2010 |

OTHER PUBLICATIONS

International Search Report and Written Opinion dated Jun. 21, 2017 for International Application No. PCT/US2017/025027.

*Primary Examiner* — Erich G Herbermann
(74) *Attorney, Agent, or Firm* — Seager, Tufte & Wickhem, LLP

(57) ABSTRACT

A stent delivery device for deploying a low column strength stent may include an inner member having a distal region and a stent receiving area disposed therein. A low column strength stent convertible between a compressed configuration and an expanded configuration may be disposed on the stent receiving area. The stent receiving area may include a soft durometer polymer configured to permit the low column strength stent to sink into the soft durometer polymer when the low column strength stent is in the compressed configuration. An outer member may be moveable between an extended position in which the outer member extends over the stent and a retracted position in which the outer member is proximal of the stent.

20 Claims, 17 Drawing Sheets

(56) References Cited

U.S. PATENT DOCUMENTS

| | | | |
|---|---|---|---|
| 5,709,703 A | 1/1998 | Lukic et al. | |
| 5,772,609 A | 6/1998 | Nguyen et al. | |
| 5,772,669 A | 6/1998 | Vrba | |
| 6,139,510 A | 10/2000 | Palermo | |
| 6,254,608 B1 * | 7/2001 | Solar | A61F 2/958 606/108 |
| 6,582,460 B1 | 6/2003 | Cryer | |
| 6,592,549 B2 | 7/2003 | Gerdts et al. | |
| 6,607,551 B1 * | 8/2003 | Sullivan | A61F 2/95 623/1.11 |
| 6,645,239 B1 | 11/2003 | Park et al. | |
| 6,884,259 B2 | 4/2005 | Tran et al. | |
| 6,902,575 B2 | 6/2005 | Laakso et al. | |
| 7,127,789 B2 | 10/2006 | Stinson | |
| 7,300,456 B2 | 11/2007 | Andreas et al. | |
| 7,468,070 B2 | 12/2008 | Henry et al. | |
| 7,473,271 B2 | 1/2009 | Gunderson | |
| 7,887,574 B2 | 2/2011 | McFerran | |
| 8,444,685 B2 | 5/2013 | Gerdts et al. | |
| 8,535,368 B2 | 9/2013 | Headley, Jr. et al. | |
| 8,668,728 B2 | 3/2014 | Headley et al. | |
| 8,764,816 B2 | 7/2014 | Koss et al. | |
| 8,834,550 B2 | 9/2014 | Leanna et al. | |
| 2002/0013599 A1 | 1/2002 | Limon et al. | |
| 2003/0033001 A1 * | 2/2003 | Igaki | A61F 2/95 623/1.11 |
| 2005/0165352 A1 | 7/2005 | Henry et al. | |
| 2007/0233224 A1 * | 10/2007 | Leynov | A61F 2/95 623/1.12 |
| 2014/0200648 A1 * | 7/2014 | Newell | A61F 2/844 623/1.11 |
| 2014/0277565 A1 | 9/2014 | Clerc | |
| 2014/0296959 A1 | 10/2014 | Leanna et al. | |

\* cited by examiner

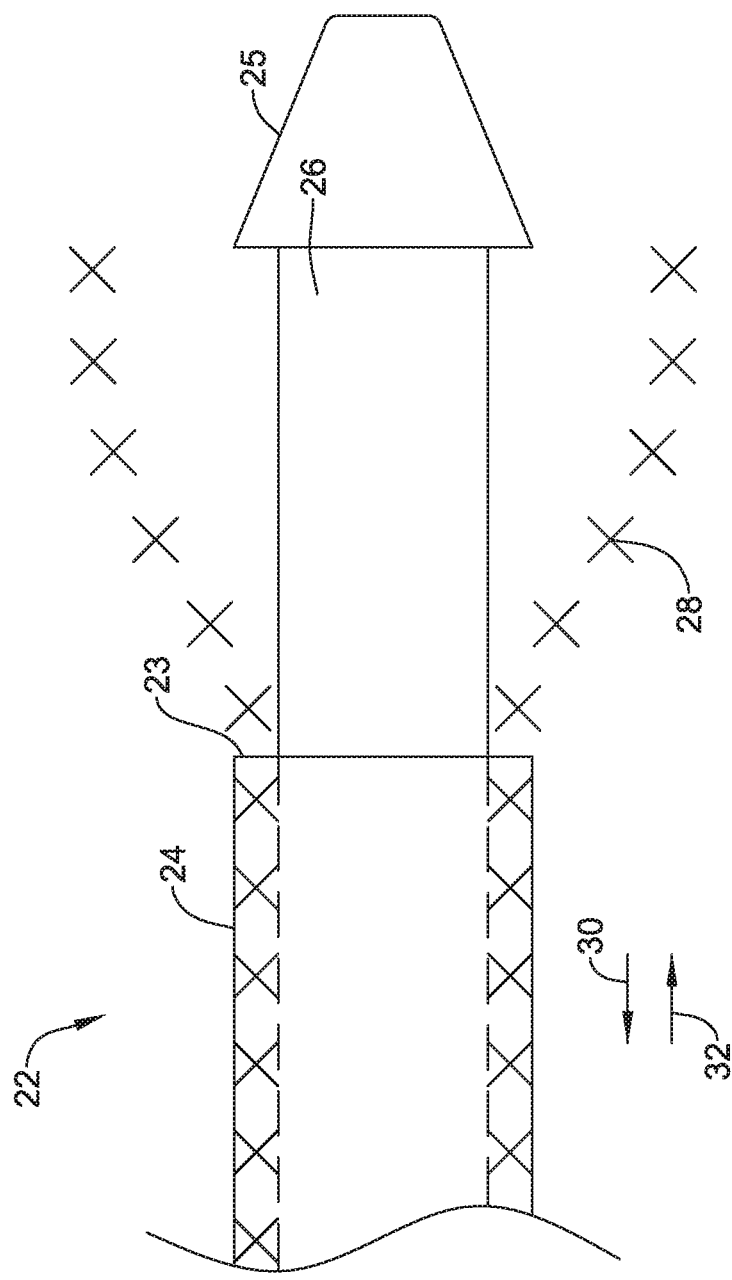

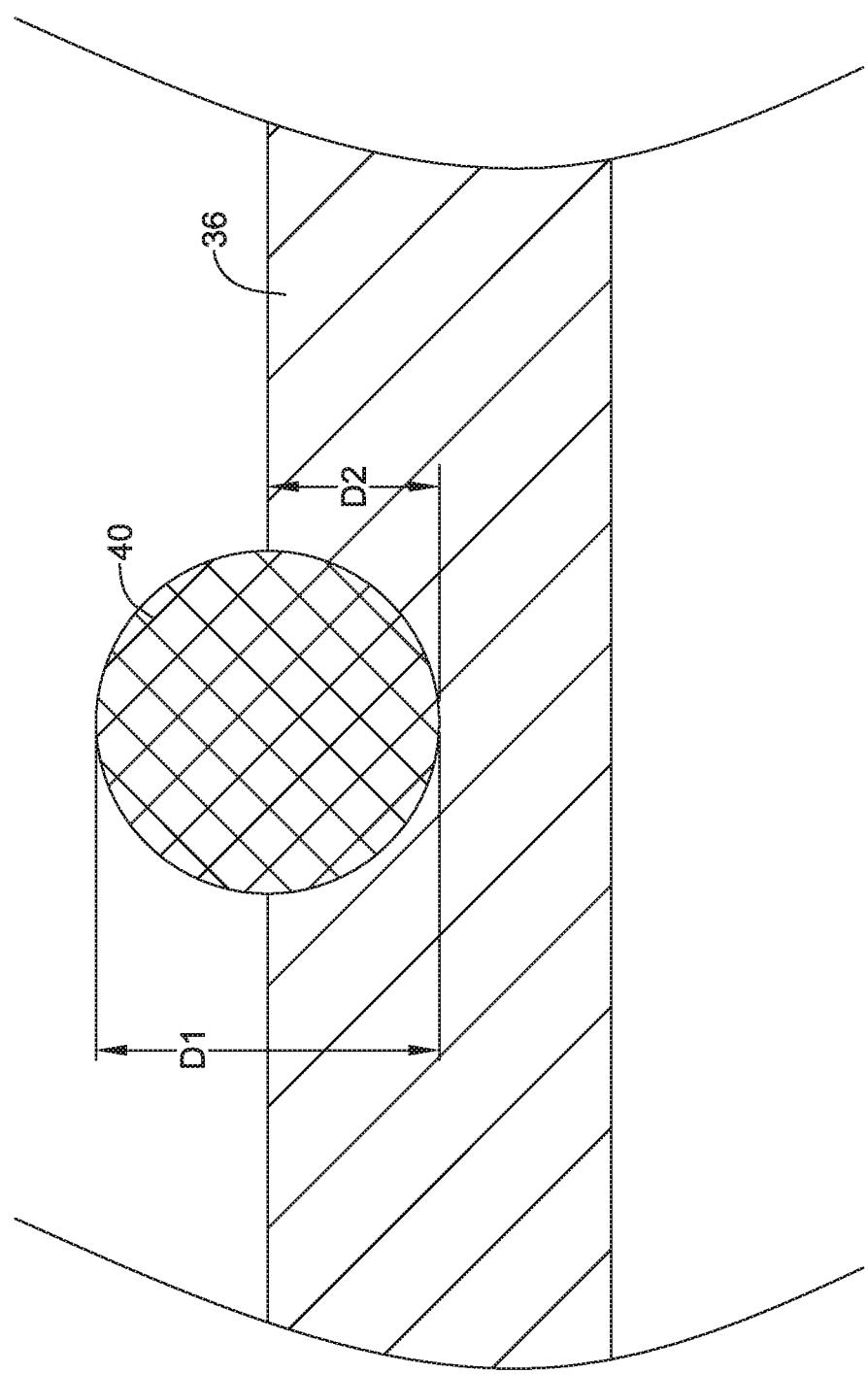

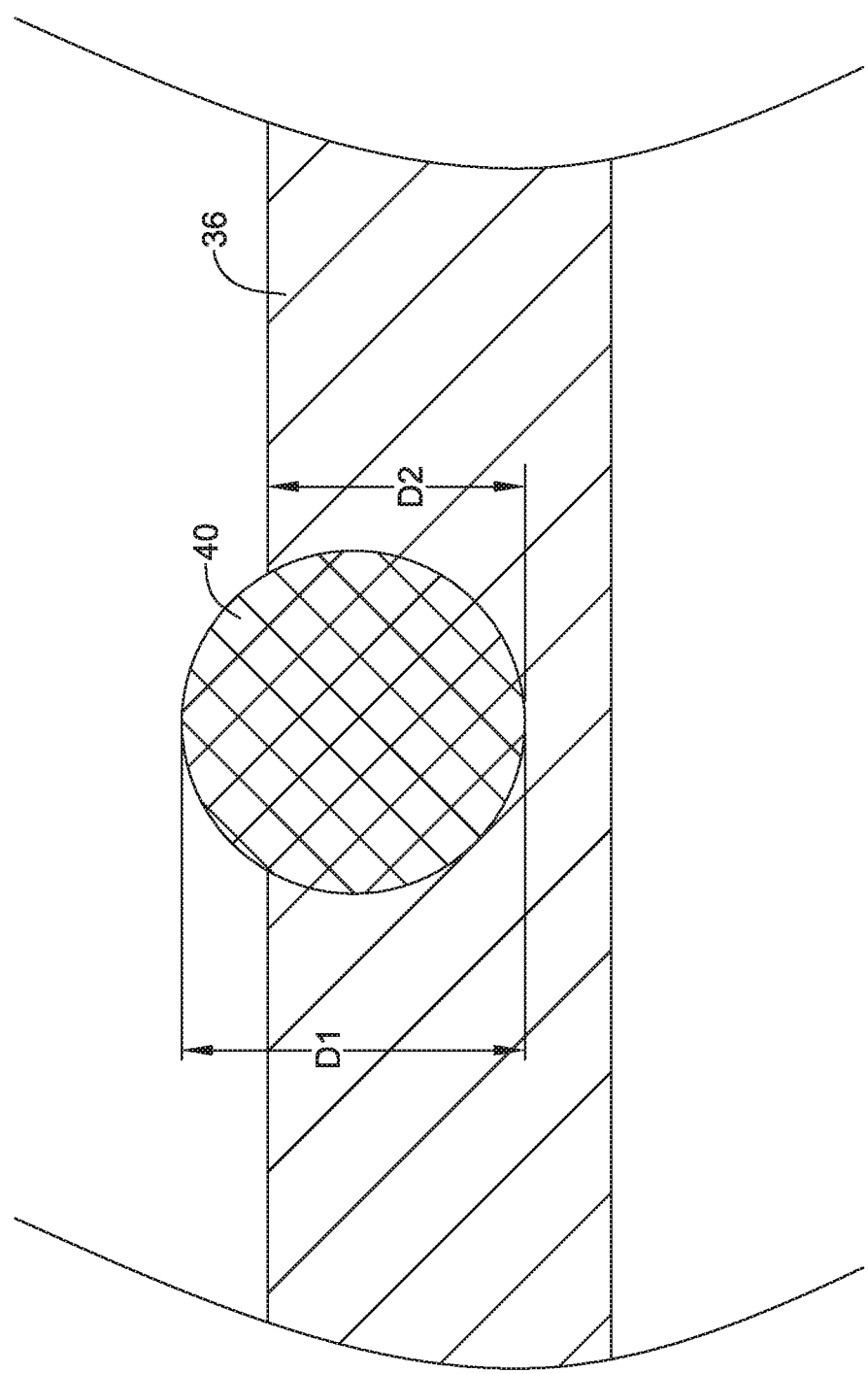

STENT DELIVERY DEVICE

CROSS REFERENCE TO RELATED APPLICATIONS

This application claims the benefit of U.S. Provisional Patent Application Ser. No. 62/318,283 filed on Apr. 5, 2016, the disclosure of which is incorporated herein by reference.

TECHNICAL FIELD

The present invention pertains to medical devices and methods for making and using medical devices. More particularly, the present invention pertains to stent delivery systems.

BACKGROUND

A wide variety of intracorporeal medical devices have been developed for medical use, for example, intravascular use. Some of these devices include stent delivery systems. These devices are manufactured by any one of a variety of different manufacturing methods and may be used according to any one of a variety of methods. Of the known stent delivery devices and methods for making and using the same, each has certain advantages and disadvantages. There is an ongoing need to provide alternative stent delivery devices as well as alternative methods for making and using stent delivery devices.

SUMMARY

The disclosure is directed to several alternative designs, materials and methods of manufacturing medical device structures and assemblies, and uses thereof. A stent delivery device for deploying a low column strength stent is disclosed.

One exemplary stent delivery device includes an inner member including a distal region, and a stent receiving area disposed within the distal region of the inner member. The device also includes a low column strength stent disposed on the stent receiving area and convertible between a compressed configuration and an expanded configuration. The stent receiving area includes a soft durometer polymer configured to permit the low column strength stent to sink into the soft durometer polymer when the low column strength stent is in the compressed configuration. The device also includes an outer member movable between an extended position in which the outer member extends over the low column strength stent and maintains the low column strength stent in the compressed configuration and a retracted position in which the outer member is proximal of the low column strength stent, permitting the low column strength stent to expand into the expanded configuration.

Alternatively or additionally to any of the embodiments above, the low column strength stent is at least partially embedded into the soft durometer polymer when the low column strength stent is in the compressed configuration.

Alternatively or additionally to any of the embodiments above, the low column strength stent comprises an esophageal stent.

Alternatively or additionally to any of the embodiments above, the low column strength stent comprises a woven stent.

Alternatively or additionally to any of the embodiments above, the low column strength stent comprises a laser cut stent.

Alternatively or additionally to any of the embodiments above, the low durometer polymer has a Shore D hardness value ranging from about 10 to about 80.

Alternatively or additionally to any of the embodiments above, the low durometer polymer includes at least one of a polyolefin, a vinyl, a silicone and a fluoropolymer.

Alternatively or additionally to any of the embodiments above, the outer member has an inner diameter and the stent receiving region of the inner member has an outer diameter, and a difference between the inner diameter of the outer member and the outer diameter of the stent receiving region of the inner member is less than a wall thickness of the low column strength stent.

A stent delivery device that is configured to laterally constrain a stent during deployment in order to help maintain a three dimensional shape of the stent is disclosed. The stent delivery device includes an inner member including a distal region, and a stent receiving area disposed within the distal region of the inner member. The stent receiving area includes a soft durometer polymer configured to laterally constrain a stent during delivery by allowing the stent to at least partially embed itself in the soft durometer polymer when the stent is in a compressed configuration. The device also includes an outer member movable between an extended position in which the outer member extends over the stent receiving area and a retracted position in which the outer member is proximal of the stent receiving area. The stent is able to maintain its three dimensional shape during deployment by virtue of the stent being at least partially embedded in the soft durometer polymer as the outer member is withdrawn proximally in order to allow the stent to expand into an expanded configuration.

Alternatively or additionally to any of the embodiments above, the soft durometer polymer permits a partially deployed stent to be recaptured by extending the outer member back over the partially deployed stent, compressing the partially deployed stent back into its compressed configuration in which the stent is at least partially embedded in the soft durometer polymer.

Alternatively or additionally to any of the embodiments above, the stent delivery device further comprises a woven stent disposed within the stent receiving area.

Alternatively or additionally to any of the embodiments above, the stent delivery device further comprises a laser cut stent disposed within the stent receiving area.

Alternatively or additionally to any of the embodiments above, the low durometer polymer has a Shore D hardness value ranging from about 10 to about 80.

Alternatively or additionally to any of the embodiments above, the low durometer polymer includes at least one of a polyolefin, a vinyl, a silicone and a fluoropolymer.

A method of delivering a low column strength stent using a stent delivery device having a compliant stent-receiving area and a deployment sheath deployable over the stent-receiving area is disclosed. The method includes advancing the stent delivery device to a stent deploying position with a low column strength stent disposed within the compliant stent receiving area, the stent in a compressed configuration in which the stent is at least partially embedded within the compliant stent receiving area. The method further includes starting to deploy the stent by withdrawing the deployment sheath proximally, allowing a portion of the stent to expand from the compressed configuration to an expanded deployment configuration. The method further includes continuing to deploy the stent by further withdrawing the deployment sheath proximally, allowing a further portion of the stent to expand from the compressed configuration to the expanded deployment configuration. The method further includes recapturing the partially deployed stent by advancing the deployment sheath distally over the partially deployed stent to compress the partially deployed stent back into the compressed configuration in which the stent is at least partially embedded within the compliant stent receiving area.

Alternatively or additionally to any of the embodiments above, the compliant stent receiving area is configured such that as the deployment sheath is advanced distally over the partially deployed stent to compressed the partially deployed stent back into the compressed configuration, the compliant stent receiving area provides a holding force on the stent that exceeds a frictional force applied to the stent via the deployment sheath.

Alternatively or additionally to any of the embodiments above, the deployment sheath is dimensioned such that as the deployment sheath is advanced distally over the partially deployed stent, the deployment sheath applies a compressive force to embed the partially deployed stent into the compliant stent receiving area.

Alternatively or additionally to any of the embodiments above, the method further comprises deploying the recaptured stent by withdrawing the deployment sheath proximally.

Alternatively or additionally to any of the embodiments above, the compliant stent receiving area comprises a polymer having a Shore D hardness value of about 10 to about 80.

Alternatively or additionally to any of the embodiments above, the low column strength stent comprises a stent that is easily distorted from its native three dimensional shape.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE FIGURES

The aspects of the disclosure may be further understood in consideration of the following detailed description of various embodiments in connection with the accompanying drawings, in which:

FIG. 4 is a partial cross-sectional view of a distal portion of the stent delivery system of FIG. 1, shown with a stent being partially deployed;

FIG. 6B is a schematic enlarged view of a portion of FIG. 6A, illustrating a relative embedding depth of the stent;

FIG. 6C is a schematic enlarged view of a portion of FIG. 6A, illustrating another relative embedding depth of the stent;

Figure 1:
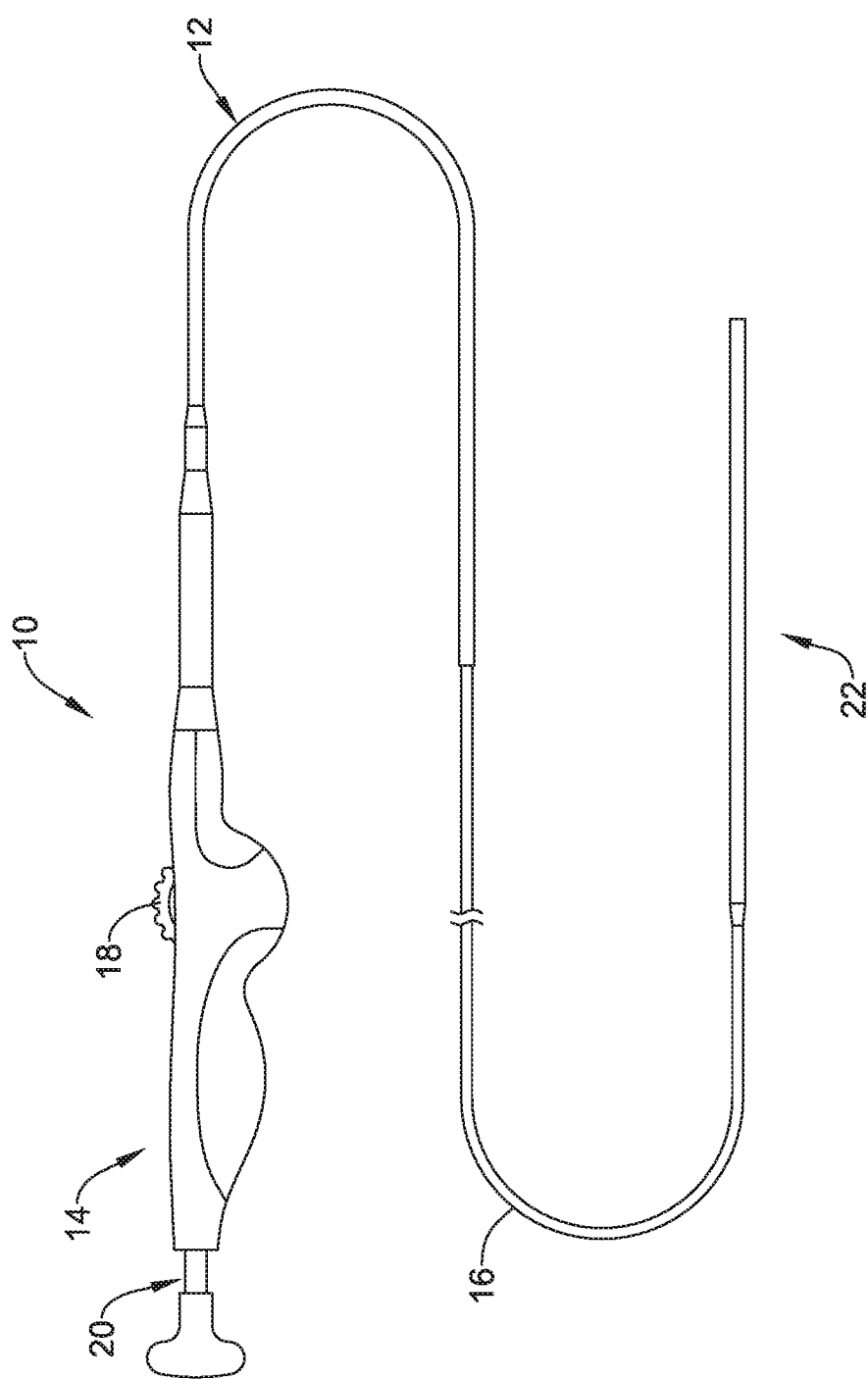
FIG. 1 is a side view of an example stent delivery system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

FIG. 1 illustrates an example stent delivery system 10. The delivery system 10 may include an elongate shaft 12 and a handle 14 coupled to shaft 12. In general, system 10 may be used to deliver a suitable stent, graft, endoprosthesis or the like to an area of interest within a body lumen of a patient. The body lumen may be a blood vessel located near the heart (e.g., within or near a cardiac vessel), within a peripheral vessel, within a neurological vessel, or at any other suitable location. Deployment of the stent may include the proximal retraction of an outer member or deployment sheath (not seen in this Figure), which overlies the stent. In some cases, the outer member or deployment sheath may be moved either distally or proximally by actuating an actuation member such as an actuation member 18 or an actuation member 20, both of which are generally disposed within the handle 14. In the example illustrated in FIG. 1, actuation member 18 is a thumb wheel that can be rotated by a clinician in order actuate the outer the outer member or deployment sheath relative to the stent. The elongate shaft 12 may include a distal region 22, shown in greater detail in FIG. 2.

Figure 2:
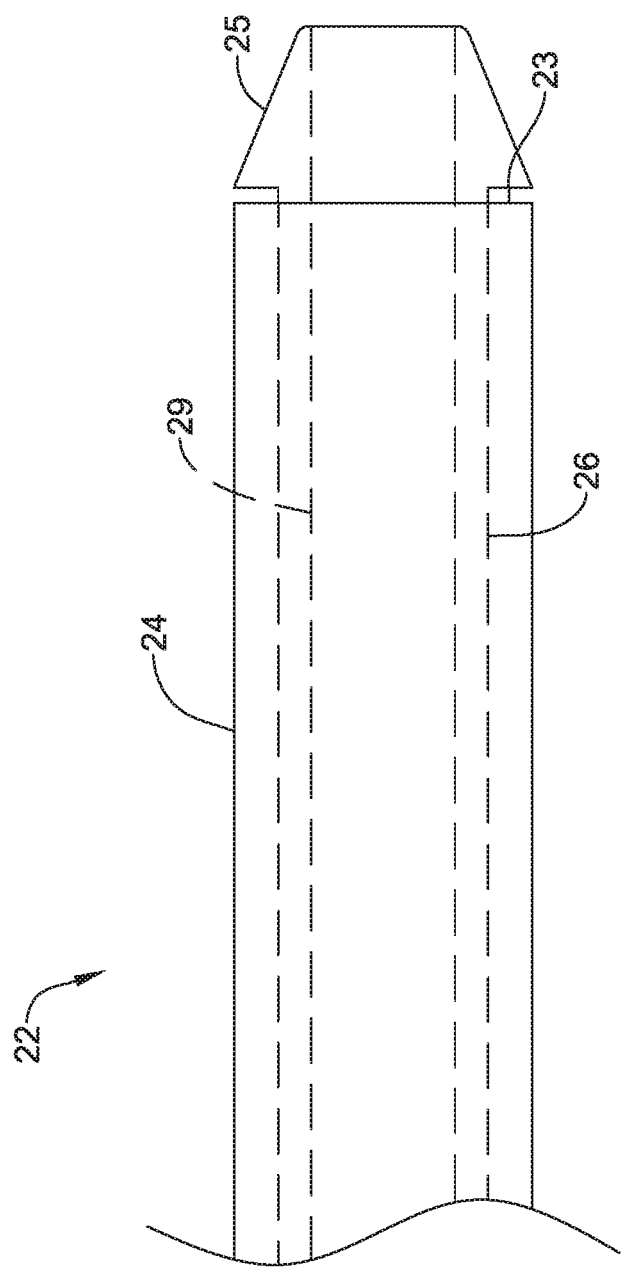
FIG. 2 is a partial cross-sectional view of a distal portion of the stent delivery system of FIG. 1.
Figure 3:
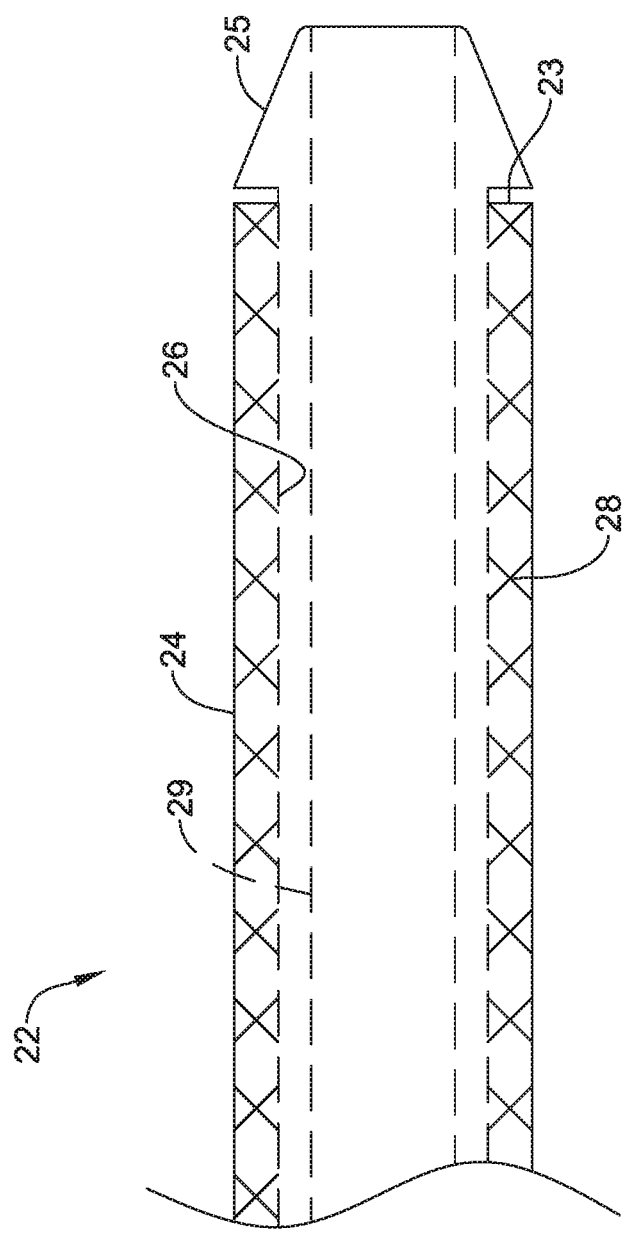
FIG. 3 is a partial cross-sectional view of a distal portion of the stent delivery system of FIG. 1.

FIG. 2 may be considered as being an enlarged partial cross-sectional view of the distal region 22 (of the elongate shaft 12). In some cases, as illustrated, the distal region 22 includes an outer member or deployment sheath 24 that is slidingly disposed over an inner member 26, which is shown in phantom extending through the lumen of the outer member or deployment sheath 24. In some cases, a stent to be deployed may be secured about the inner member 26 and constrained in a compressed configuration within the lumen of the deployment sheath 24 for delivery via the deployment sheath 24. In some instances, the inner member 26 may include an atraumatic tip 25 at a distal end of the inner member 26 located distal of the distal end of the outer member 24. In some cases, while not illustrated, a distal end 23 of the deployment sheath 24 may include an atraumatic tip. In some instances, the inner member 26 may be a tubular member including a lumen 29, such as a guidewire lumen, extending therethrough. A stent 28, which may for example be a braided stent, a knitted stent, a woven stent or a laser cut stent, is shown in phantom in FIG. 3. In some cases, the stent 28 may be an esophageal stent, but this is not required.

Turning to FIG. 4, the stent 28 has been partially deployed by moving the deployment sheath 24 in a proximal direction relative to the stent 28 and the inner member 26. The stent 28 may be considered as being a self-expanding stent, meaning that once unconstrained, the stent 28 will automatically expand from a compressed configuration to an expanded configuration. As can be seen, a distal end region of the stent 28 begins to expand as soon as the distal end region of the stent 28 is no longer constrained by the deployment sheath 24. While shown partially deployed, it will be appreciated that as the deployment sheath 24 is moved further in a proximal direction as indicated by an arrow 30, more and more of the stent 28 will regain its expanded configuration, until the entire stent 28 has been exposed, and thus unconstrained by the deployment sheath 24.

In some cases, the stent 28 may be configured such that it has a low column strength, meaning for example that it is easily deformed or otherwise altered from a native three dimensional shape of the stent 28, or that the stent 28 contains certain sections, individual components (e.g., filaments), or regions that are permitted to slide or move relative to adjacent sections, individual components (e.g., filaments), or regions at least partially along the longitudinal length of the stent 28 when the stent 28 is deployed. In some instances, for example, the frictional forces between the deployment sheath 24 and the stent 28, caused by pulling the deployment sheath 24 proximally to release the stent 28 can itself stretch or pull individual components (e.g., filaments) of the stent 28, such as individual windings and/or filaments, relative to other individual components (e.g., filaments) of the stent 28, thereby causing the stent 28 to stretch or otherwise deform from a native or otherwise intended three dimensional shape of the stent 28. In some cases, the forces applied to the stent 28 by moving the deployment sheath 24 in a distal direction as indicated by an arrow 32, such as for example if there is a desire to recapture the stent 28 after partial deployments in order to move it prior to redeployment, can cause further deformation of the stent 28. In some instances, the frictional force between the stent 28 and the deployment sheath 24 may be about 8.9 N to about 17.8 N (2 lbf to about 4 lbf), for example, whereas, the column strength of the stent 28 in its constrained configuration may be less than 17.8 N (4 lbf), less than 13.3 N (3 lbf), or less than 8.9 N (2 lbf). In other words, the column strength of the stent 28 in the constrained configuration may be sufficiently low such that the length of the stent 28 will be longitudinally stretched (e.g., filament segments move longitudinally relative to adjacent filament segments) when subjected to an axial force of greater than 8.9 N (2 lbf), greater than 13.3 N (3 lbf), or greater than 17.8 N (4 lbf) caused by frictional forces between the stent 28 and the deployment sheath 24 as the deployment sheath 24 is pulled proximally off of the stent 28 to deploy the stent 28 and/or the length of the stent 28 will be longitudinally collapsed (e.g., filament segments move longitudinally relative to adjacent filament segments) when subjected to an axial force of greater than 8.9 N (2 lbf), greater than 13.3 N (3 lbf), or greater than 17.8 N (4 lbf) caused by frictional forces between the stent 28 and the deployment sheath 24 as the deployment sheath 24 is pushed distally over the stent 28 to recapture the stent 28.

Accordingly, in some cases the inner member 26 may be configured to help maintain the three dimensional shape of the stent 28 during deployment, recapturing and/or redeployment. In some cases, for example, maintaining the three dimensional shape of the stent 28 may be defined in terms of percent elongation (stretching), referring to a change in length relative to a nominal length during deployment, recapture and/or redeployment. For example, it may be reasonable to define a percent of elongation that is less than about ten percent, or in some cases less than about five percent. In some cases, maintaining the three dimensional shape of the stent 28 may be defined in terms of percent compression, referring to a change in length relative to a nominal length during deployment, recapture and/or deployment. For example, it may be reasonable to define a percent of compression that is less than about ten percent, or in some cases less than about five percent. Another way to consider maintaining the three dimensional shape of the stent 28 may be to state that the stent 28 retains about 95% to about 105% of its length during deployment, recapture and/or deployment. It will be appreciated that as the stent 28 changes in length, it may also change in radius. As the stent 28 elongates, the radius of the stent 28 may correspondingly decrease. Conversely, if the stent 28 shortens, the radius of the stent 28 may correspondingly increase.

Figure 5A:
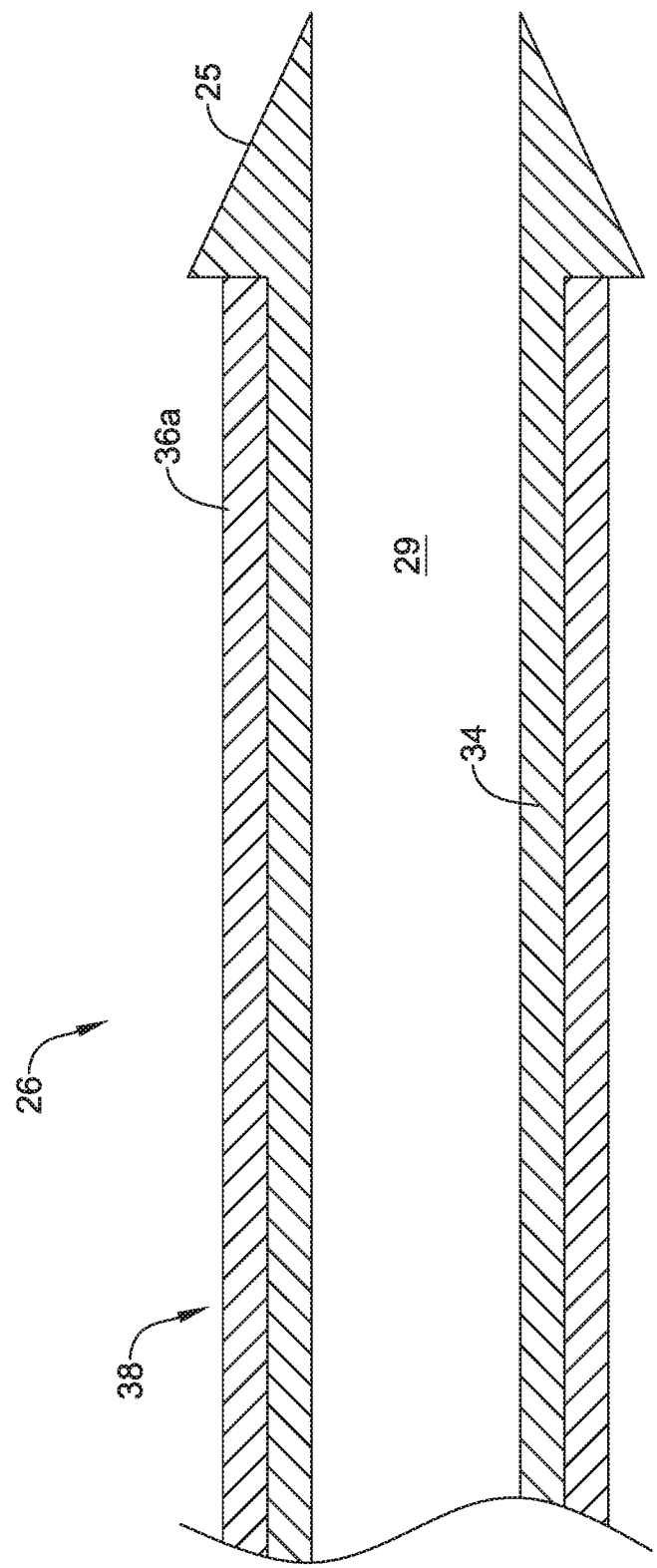
FIG. 5A is a side view of an inner member forming part of the distal portion of FIGS. 3 and 4.
Figure 5B:
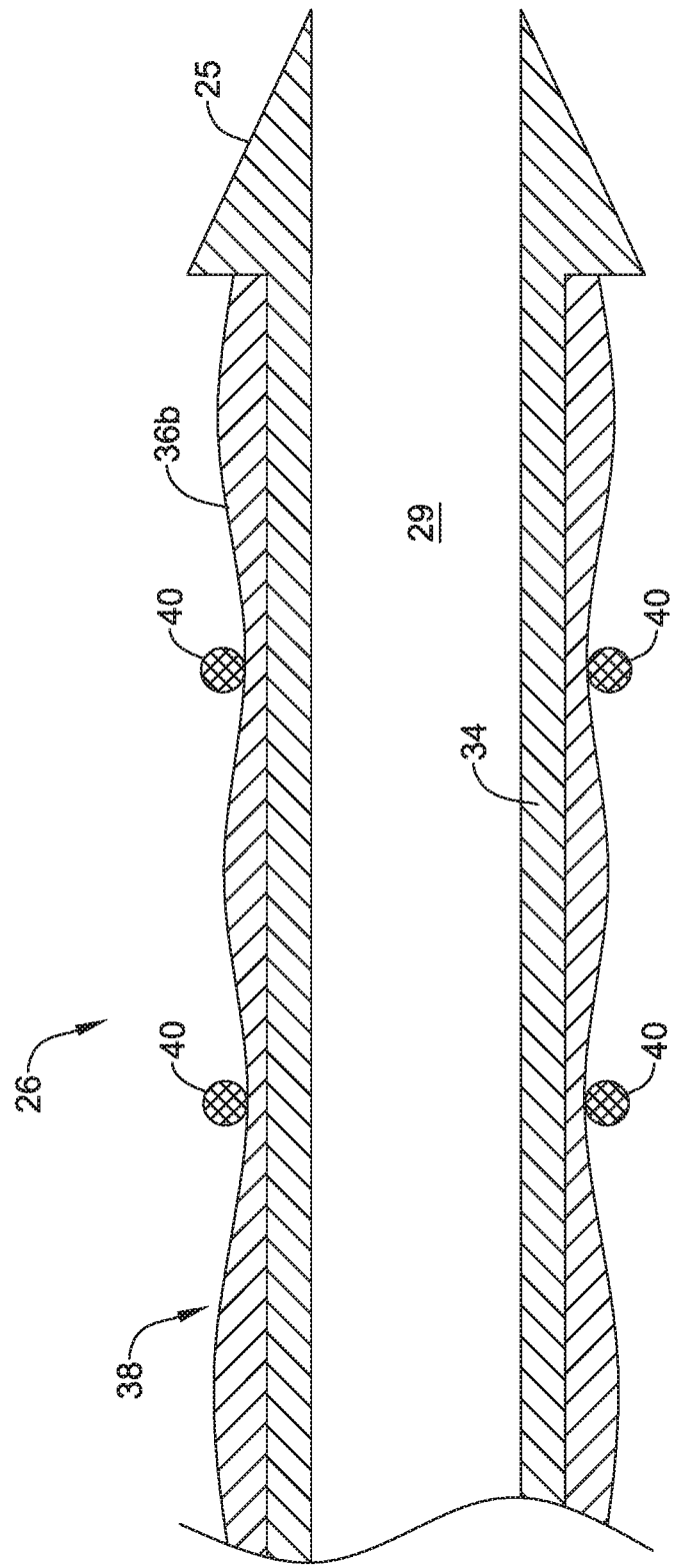
FIG. 5B is a side view of an inner member illustrating another polymer layer configuration.
Figure 5C:
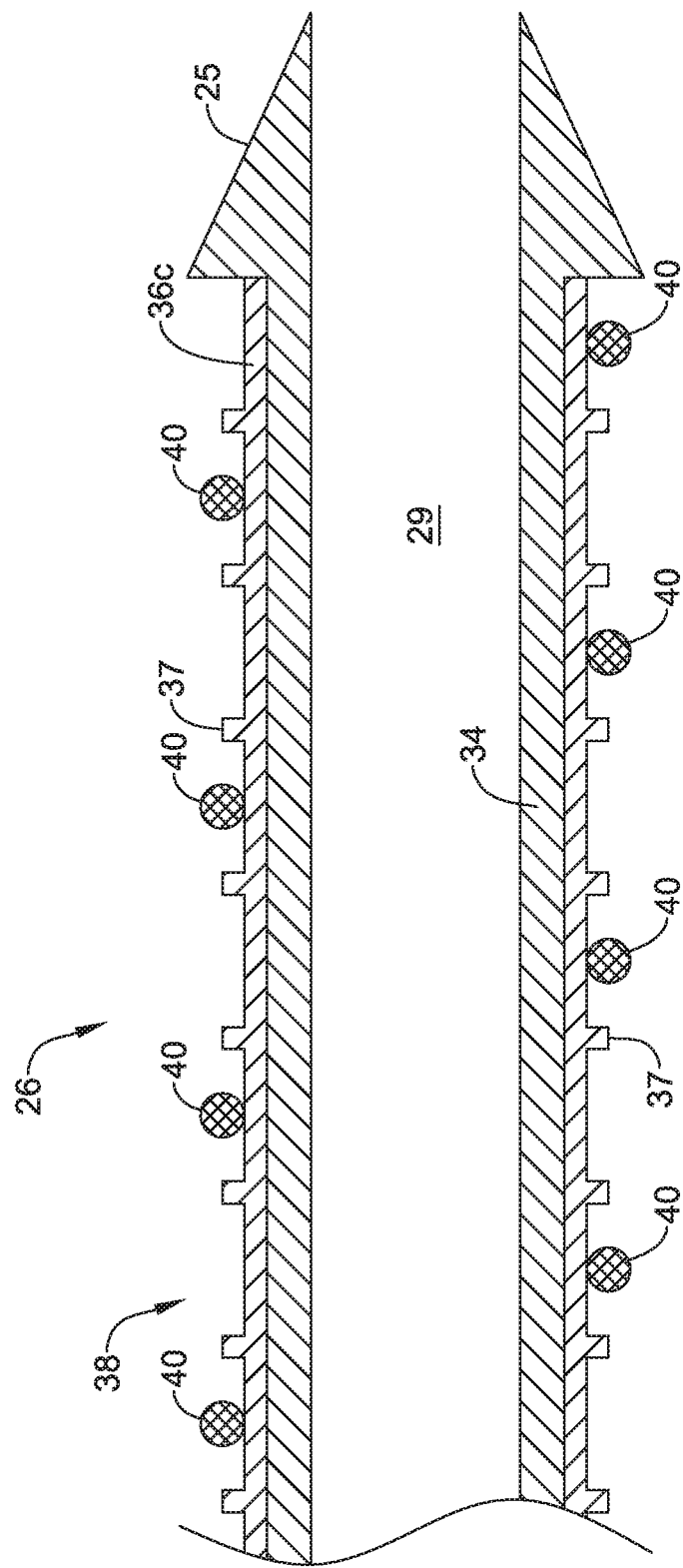
FIG. 5C is a side view of an inner member illustrating another polymer layer configuration.
Figure 5D:
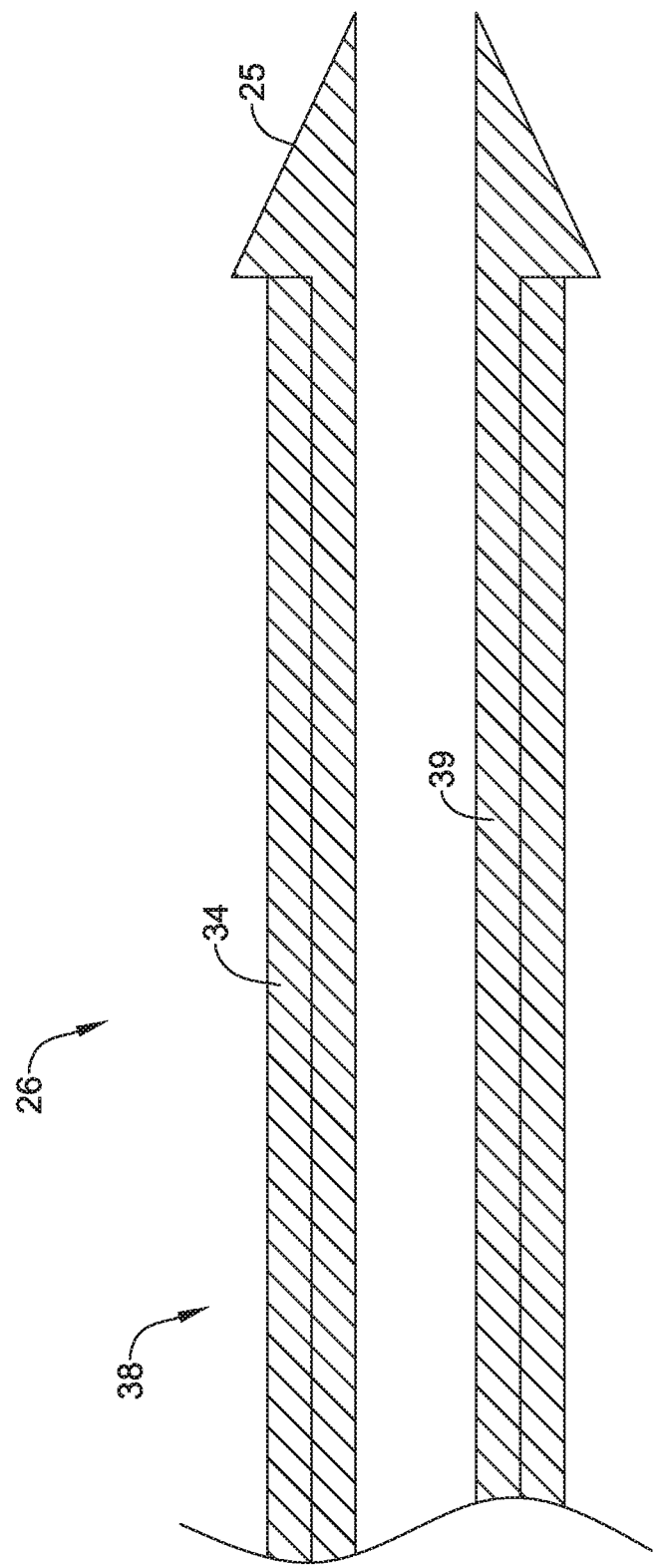
FIG. 5D is a side view of an inner member illustrating another polymer layer configuration.

As seen in FIG. 5A, which is a cross-sectional view of the inner member 26, the inner member 26 may include a shaft 34 and a polymeric coating or layer 36a. The inner member 26 may be considered as including a stent receiving area 38. In some cases, the stent receiving area 38 may include a portion of the polymeric layer 36a. In some instances, the polymeric layer 36 may essentially form the stent receiving area 38. In FIG. 5A, the polymeric layer 36a is shown as having a smooth outer surface, with a relatively constant outer diameter. In some cases, the polymeric layer 36a may have other configurations. For example, in FIG. 5B, a polymeric layer 36b has an undulating or wave-like outer surface configuration. In some cases, individual windings or filaments 40 of the stent 28 may, for example, fit into valleys or low spots in the undulating polymeric layer 36b between adjacent peaks or high spots in the undulating polymeric layer 36b. FIG. 5C shows a polymeric layer 36c that includes a plurality of fingers 37 that extend outward from the polymeric layer 36c. In some cases, individual windings or filaments 40 of the stent 28 may fit between adjacent fingers 37. While FIG. 5C is a cross-sectional view, it will be appreciated that the polymeric layer 36c may include a plurality of fingers 37 that are axially spaced along the shaft 34 as well as being radially spaced about the shaft 34. FIG. 5D illustrates another configuration in which the polymer layer is divided into distinct strips 39. While two strips 39 are illustrated, it will be appreciated that any number of individual strips 39 may be used. While the strips 39 are illustrated as being axially aligned, in some cases the strips 39 may be radially aligned, helically aligned, and the like.

In some cases, the polymeric layer 36a, 36b, 36c may be a soft durometer polymer such as a polyolefin, a vinyl, a fluoropolymer or a silicone. In some instances, the polymeric layer 36a, 36b, 36c may be formed of a polymer having a Shore D hardness value in the range of about 10 to about 80, or a range of about 20 to about 70, or a range of about 30 to about 60, or a range of about 40 to about 50, where the Shore D hardness value is determined using known testing procedures. While the polymer layer 36a, 36b, 36c is shown in FIGS. 5A, 5B, 5C and 5D as being applied to an outer surface of the shaft 34, it will be appreciated that in some cases the polymeric layer 36a, 36b, 36c may be inset into an outer surface of the shaft 34. In some cases, the inner member 26 may itself be formed of the soft durometer polymer.

In some cases, the polymeric layer 36a, 36b, 36c may be soft enough to enable the stent 28 to be at least partially embedded within the polymeric layer 36a, 36b, 36c when the stent 28 is in its compressed configuration. In some instances, the deployment sheath 24 may be dimensioned, relative to the inner member 26, such that the deployment sheath 24 pushes the stent 28 into the polymeric layer 36a, 36b, 36c. For example, in some cases, a difference between an inner diameter of the deployment sheath 24 and an outer diameter of the polymer layer 36a, 36b, 36c of the inner member 26 may be less than a wall thickness of the stent 28. Accordingly, when the stent 28 is positioned within the lumen of the deployment sheath 24 and surrounding the polymer layer 36a, 36b, 36c of the inner member 26, the stent 28 may be pressed into the polymer layer 36a, 36b, 36c, thereby deforming and/or displacing a portion of the polymer layer 36.

Figure 6A:
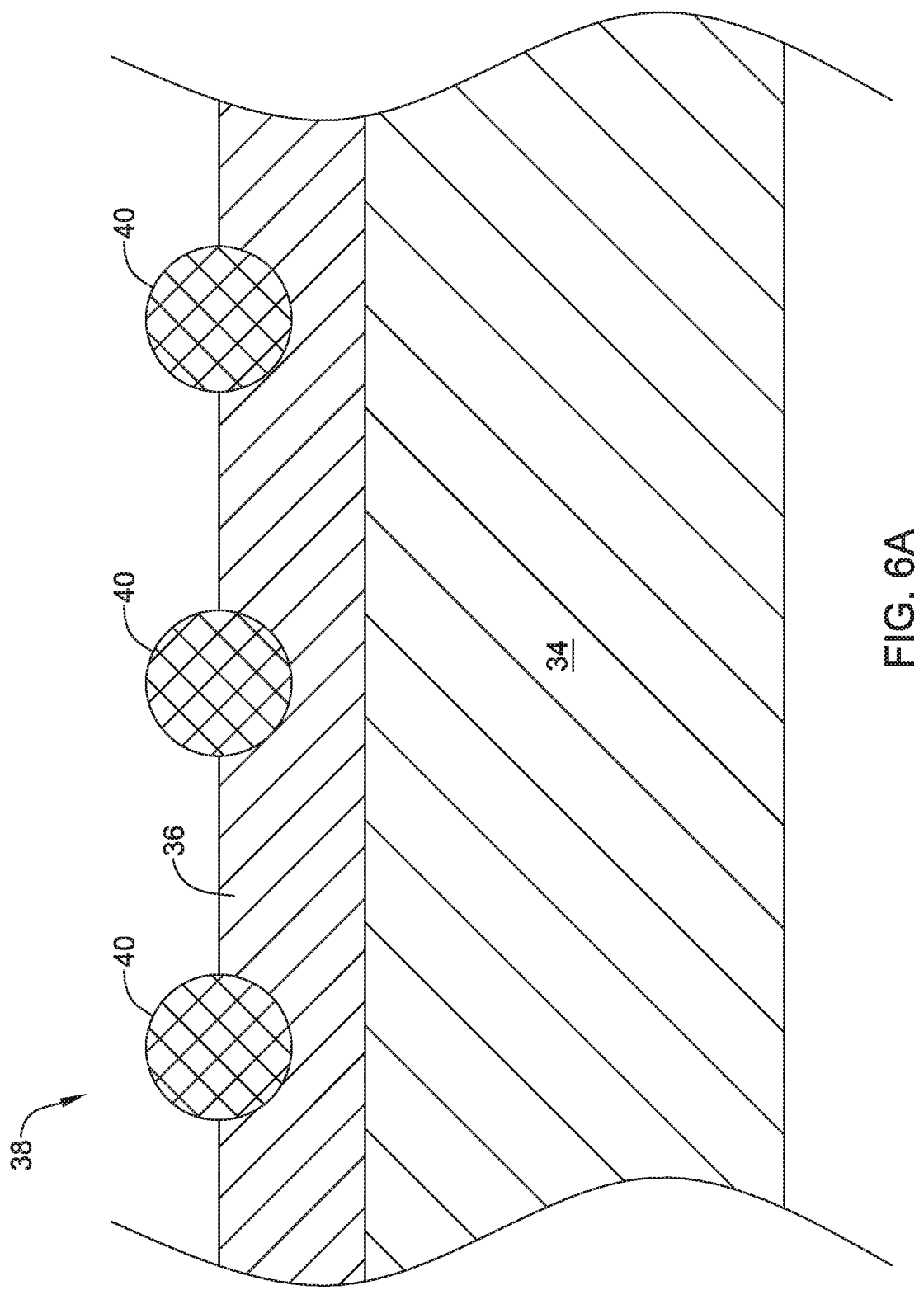
FIG. 6A is an enlarged cross-sectional view of the inner member shown in FIG. 5, in combination with a stent.

It will be appreciated that embedding the stent 28 at least partially into the polymeric layer 36a, 36b, 36c will be beneficial both in helping to hold the stent 28 in place as the deployment sheath 24 is moved proximally or distally relative to the inner member 26 (and thus relative to the stent 28) as well as helping the stent 28 to resist applied forces that would otherwise tend to longitudinally stretch, longitudinally compress or otherwise deform the stent 28. In some cases, this may be considered as laterally constraining the stent 28 in order to maintain its three dimensional shape. FIG. 6A is a cross-sectional view of a portion of the stent receiving area 38, showing individual filaments, windings, struts or other stent components 40 partially embedded into the polymeric layer 36a, 36b, 36c.

It will be appreciated that in some cases the stent 28 may be farther embedded into the polymeric layer 36a, 36b, 36c while in other cases the stent 28 may be relatively less embedded into the polymeric layer 36a, 36b, 36c. FIGS. 6B and 6C are enlarged views of a single stent component 40 embedded into a polymeric layer generically identified as polymeric layer 36. A dimension $D_1$ may be considered as being a radial thickness (e.g., diameter) of the stent component 40 measured from an radially inner surface of the stent component 40 to a radially outer surface of the stent component 40 while a dimension $D_2$ may be considered as indicating a distance that the stent component 40 has been embedded into the polymeric layer 36. A ratio between $D_1$ and $D_2$, such as $D_2/D_1$, may define a level of embedding. In FIG. 6B, the stent component 40 is not as deeply embedded as in FIG. 6C. This may, for example, be a result in a different durometer polymer being used for the polymeric layer 36. This may also result, at least in part, from a different sized stent and thus a different value for $D_1$. Accordingly, the ratio $D_2/D_1$ will be relatively smaller in the situation shown in FIG. 6B and relatively larger in the situation shown in FIG. 6C. In some cases, the ratio $D_2/D_1$ may vary from about 0.1, indicating a relatively small level of embedding, to about 1.0, indicating that the stent 28 is completely embedded. In some cases, the ratio $D_2/D_1$ may vary from about 0.2 to about 0.8, or about 0.3 to about 0.7, or about 0.4 to about 0.5. In some cases it may be desirable to have the stent component 30 embedded into the polymer layer 36 at least one-half or greater than one-half of the radial thickness (e.g., diameter) of the stent component 40 measured from an radially inner surface of the stent component 40 to a radially outer surface of the stent component 40 (i.e., $D_2 \geq D_1/2$). The degree that the stent component 40 is embedded in the polymer layer 36 may prevent the stent component 40 from moving axially relative to the polymer layer 36 during deployment, recapturing, and/or redeployment of the stent 28.

Figure 7A:
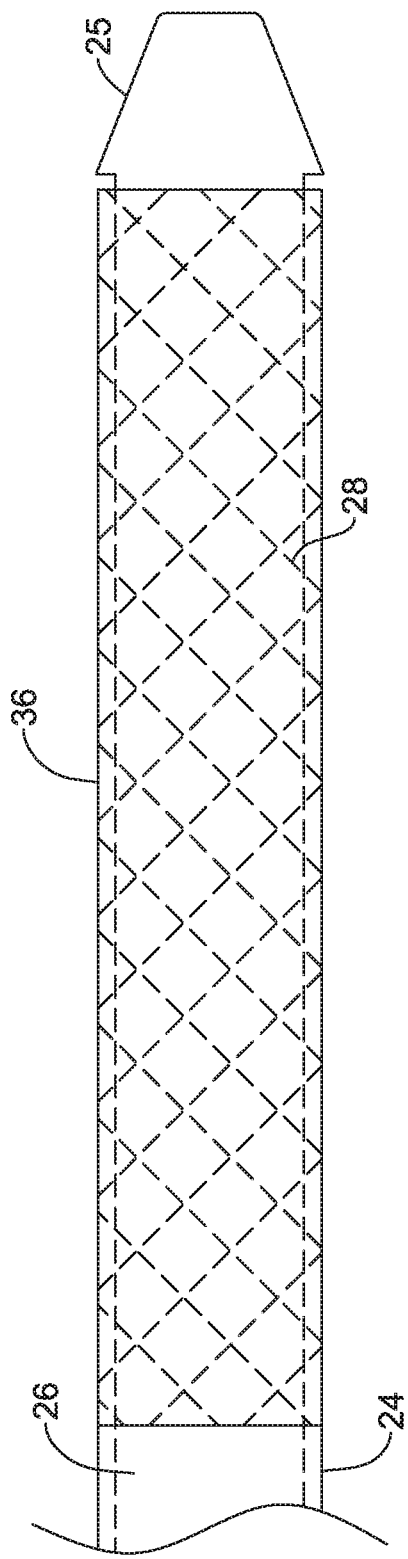
FIGS. 7A through 7C provide an illustrative but non-limiting example of deploying a low column strength stent.
Figure 7B:
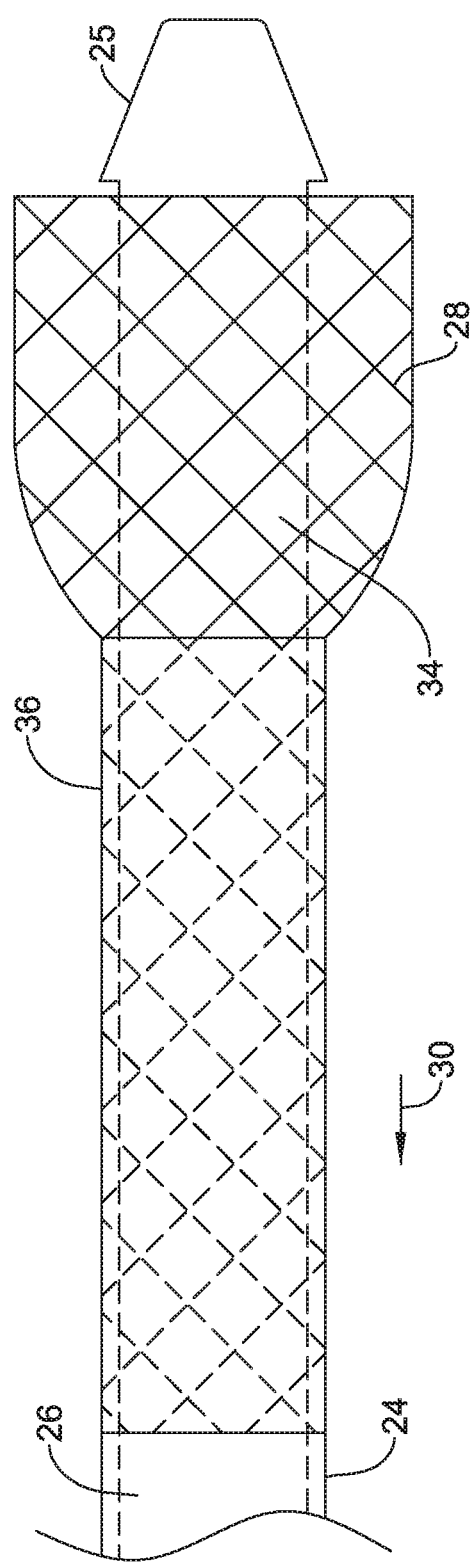
Figure 7C:
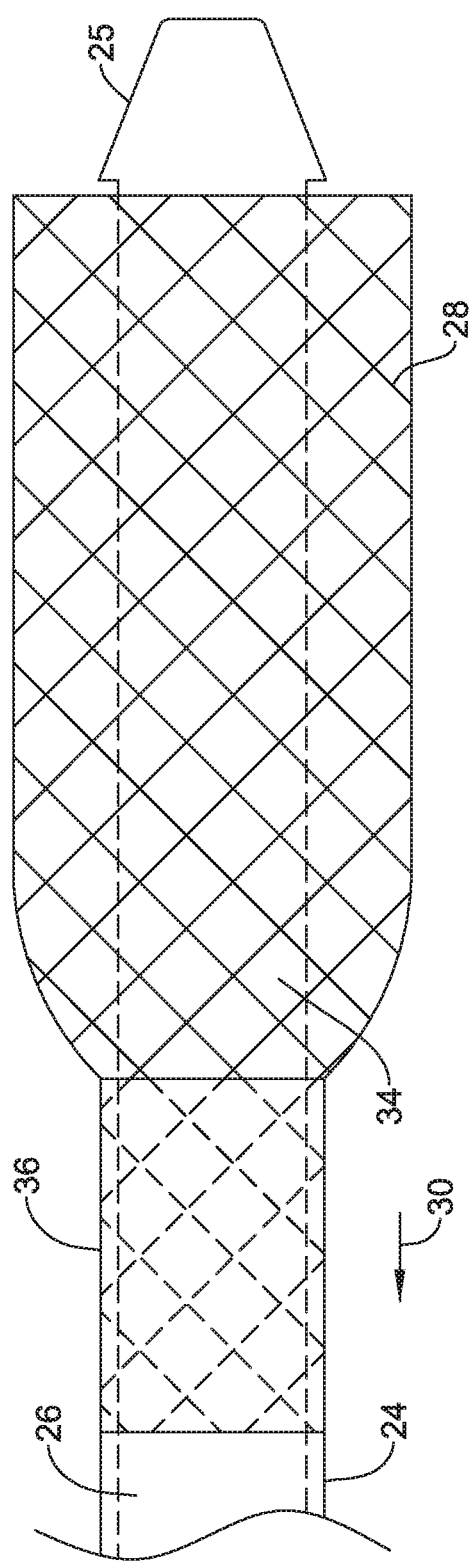

FIGS. 7A through 7C provide an illustrative but non-limiting example of deploying a low column strength stent such as the stent 28. In FIG. 7A, the stent 28 is seen disposed over the inner member 26, in a compressed configuration, with the deployment sheath 24 (for simplicity shown as being transparent) disposed over the stent 28, thereby holding the stent 28 in the compressed configuration. While not clearly shown, it is anticipated that the stent 28 is at least partially embedded into the soft durometer polymer that, as discussed for example with respect to FIG. 5, forms at least an outer surface of the inner member 26. Moving to FIG. 7B, the deployment sheath 24 has been moved proximally, in the direction indicated by the arrow 30. As can be seen, a portion of the stent 28, freed from constrainment by the deployment sheath 24, has begun to expand into its expanded configuration. A portion of the polymeric layer 36 can be seen under the expanded portion of the stent 28. Moving to FIG. 7C, it can be seen that the stent 28 has been almost completely deployed as the deployment sheath 24 has been withdrawn further proximally relative to the stent 28.

Figure 8A:
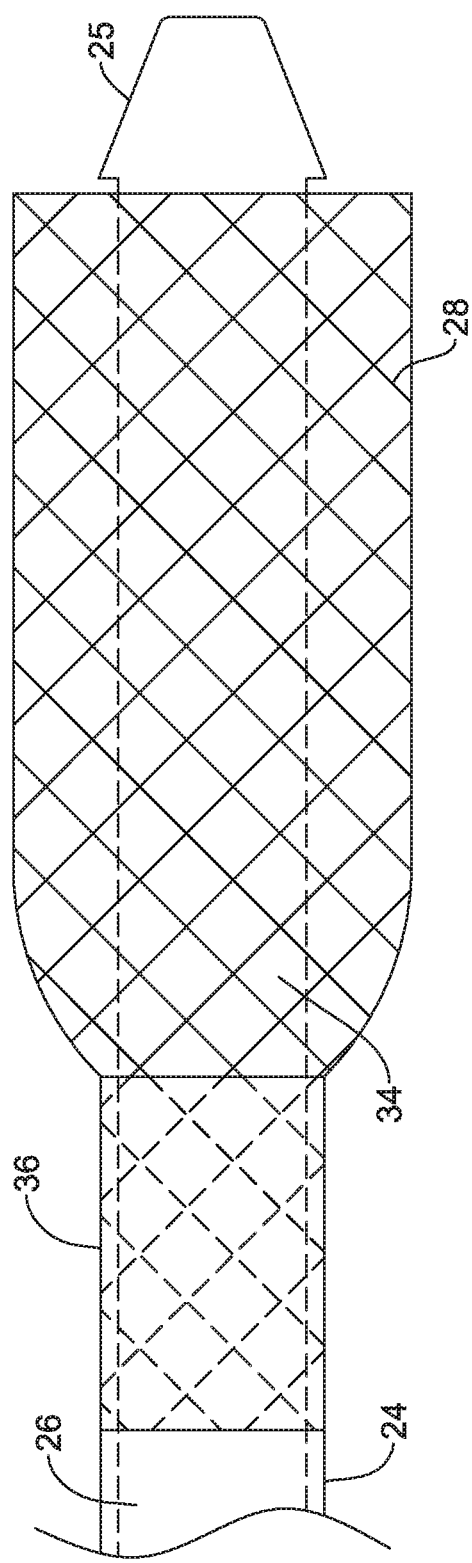
FIGS. 8A through 8C provide an illustrative but non-limiting example of recapturing a low column strength stent that has been partially deployed.
Figure 8B:
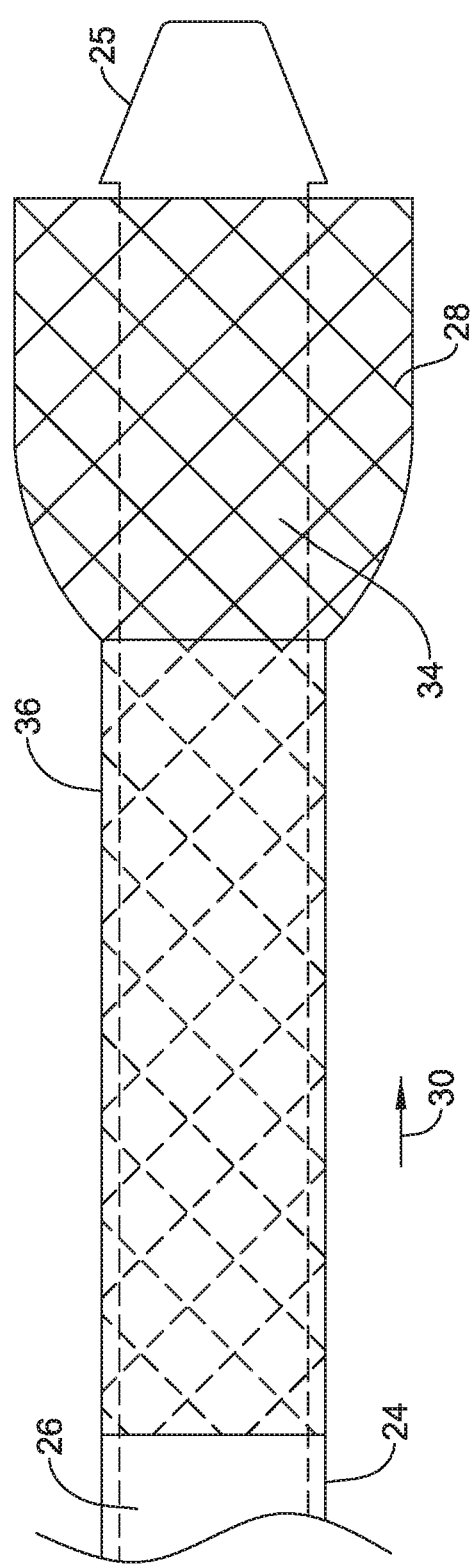
Figure 8C:
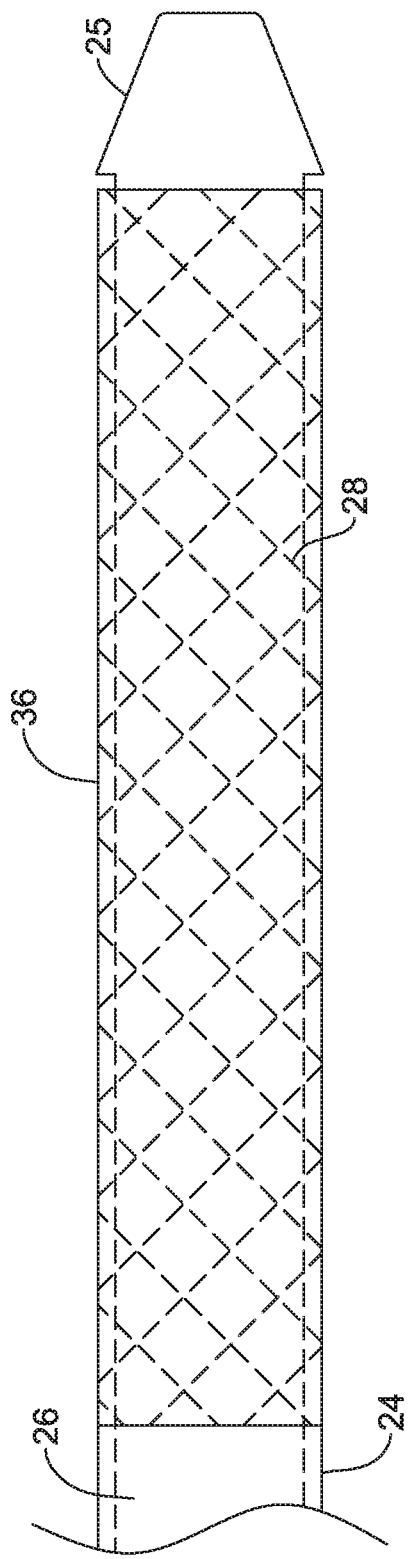

FIGS. 8A through 8C provide an illustrative but non-limiting example of recapturing a low column strength stent such as the stent 28. In some cases, there may be a desire to recapture a partially deployed stent in order to move the stent axially and/or rotationally prior to fully and finally deploying the stent 28. FIG. 8A is similar to FIG. 7C, and shows the stent 28 as being substantially (but not completely) deployed. Moving to FIG. 8B, it can be seen that the deployment sheath 24 has been moved distally relative to the stent 28, in the direction indicated by the arrow 32. As the deployment sheath 24 moves distally relative to the stent 28, the deployment sheath 24 compresses the stent 28 back down into its compressed configuration, and at least partially embeds the stent 28 into the polymer layer 36. As a result, the polymer layer 36 helps maintain the native three dimensional shape of the stent 28, and the holding forces provided by the embedded elements of the stent 28 are at least as strong if not stronger than any frictional forces created between the moving deployment sheath 24 and the stent 28. Moving to FIG. 8C, the stent 28 has been almost completely recaptured, so that it can be repositioned and redeployed, or perhaps completely removed if, for example, a decision is made that a different size or type of stent is more appropriate for a particular physiology.

Various components of the stent deployment system 10, as well as the stent 28, may be made from a metal, metal alloy, polymer (some examples of which are disclosed below), a metal-polymer composite, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In at least some embodiments, portions or all the stent deployment system 10 may also be doped with, made of, or otherwise include a radiopaque material including those listed herein or other suitable radiopaque materials.

In some embodiments, a degree of MRI compatibility is imparted into system 10. For example, to enhance compatibility with Magnetic Resonance Imaging (MRI) machines, it may be desirable to make part or all of the stent deployment system 10 in a manner that would impart a degree of MRI compatibility, such as by using materials that do not substantially distort the image and create substantial artifacts (artifacts are gaps in the image). Certain ferromagnetic materials, for example, may not be suitable because they may create artifacts in an MRI image. Portions of the stent deployment system 10 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers that may be used include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6% LCP.

In some embodiments, the exterior surface of the system 10 may include a coating, for example a lubricious, a hydrophilic, a protective, or other type of coating. Hydrophobic coatings such as fluoropolymers provide a dry lubricity which improves device handling and exchanges. Lubricious coatings improve steerability and improve lesion crossing capability. Suitable lubricious polymers may include silicone and the like, polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, the entire disclosures of which are incorporated herein by reference.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A stent delivery device for deploying a low column strength stent, the stent delivery device comprising:
   an inner member including a distal region;
   a stent receiving area having a length defined within the distal region of the inner member, the stent receiving area defined by an outer surface of the inner member extending continuously along the entire length of the stent receiving area;
   a low column strength stent formed of a plurality of stent components disposed on the stent receiving area and convertible between a compressed configuration and an expanded configuration, wherein the low column strength stent has a wall thickness measured from a radially inner surface of a single stent component to a radially outer surface of the single stent component, wherein the length of the stent receiving area extends along an entire length of the stent;
   the stent receiving area including a soft durometer polymer defining a radially outward facing surface extending continuously along the entire length of the stent receiving area, the outward facing surface of the soft durometer polymer compressed radially inward by the low column strength stent and deformed around the plurality of stent components of the low column strength stent to permit the low column strength stent to sink into the soft durometer polymer with deformed portions of the radially outward facing surface pressed against the inner surface of the plurality of stent components of the low column strength stent and become embedded into the soft durometer polymer to a level of at least one-half or greater than one-half of the wall thickness of the low column strength stent when the low column strength stent is in the compressed configuration; and
   an outer member movable between an extended position in which the outer member extends over the low column strength stent and maintains the low column strength stent in the compressed configuration within a lumen of the outer member and a retracted position in which the outer member is proximal of the low column strength stent, permitting the low column strength stent to expand into the expanded configuration.

2. The stent delivery device of claim 1, wherein the low column strength stent comprises an esophageal stent.

3. The stent delivery device of claim 1, wherein the low column strength stent comprises a woven stent.

4. The stent delivery device of claim 1, wherein the low column strength stent comprises a laser cut stent.

5. The stent delivery device of claim 1, wherein the soft durometer polymer has a Shore D hardness value ranging from about 10 to about 80.

6. The stent delivery device of claim 1, wherein the soft durometer polymer includes at least one of a polyolefin, a vinyl, a silicone and a fluoropolymer.

7. The stent delivery device of claim 1, wherein the outer member has an inner diameter and the stent receiving region of the inner member has an outer diameter, and a difference between the inner diameter of the outer member and the outer diameter of the stent receiving region of the inner member is less than the wall thickness of the low column strength stent.

8. The stent delivery device of claim 1, wherein the low durometer stent, in its constrained configuration, has a column strength less than 17.8 N (4 lbf).

9. The stent delivery device of claim 1, wherein the inner member has a distal tip with an outer diameter greater than a diameter of the lumen of the outer member, wherein when the outer member is in the extended position, a distal end of the outer member abuts the distal tip.

10. A stent delivery device configured to laterally constrain a stent during deployment in order to help maintain a three dimensional shape of the stent, the stent delivery device comprising:
   an inner tubular member including a distal region, the inner tubular member having a lumen configured to receive a guidewire;
   a stent receiving area having a length defined within the distal region of the inner tubular member, the stent disposed within the stent receiving area such that the length of the stent receiving area extends along an entire length of the stent, the stent receiving area including a soft durometer polymer defining a radially outward facing surface extending continuously along the entire length of the stent receiving area, the soft durometer polymer configured to laterally constrain the stent during delivery by allowing the stent to at least partially embed itself in the soft durometer polymer to a level of at least one-half or greater than one-half of a wall thickness of the stent when the stent is in a compressed configuration; and
   an outer member movable between an extended position in which the outer member extends over the stent receiving area and a retracted position in which the outer member is proximal of the stent receiving area;
   wherein the inner tubular member has a constant outer diameter along the entire length of the stent receiving area and extending proximal of the stent receiving area;
   wherein the stent is able to maintain its three dimensional shape during deployment by virtue of the stent being at least partially embedded in the soft durometer polymer as the outer member is withdrawn proximally in order to allow the stent to expand into an expanded configuration.

11. The stent delivery device of claim 10, wherein the soft durometer polymer permits the stent when partially deployed to be recaptured by extending the outer member back over the partially deployed stent, compressing the partially deployed stent back into its compressed configuration in which the stent is at least partially embedded in the soft durometer polymer.

12. The stent delivery device of claim 10, wherein the stent is a woven stent disposed within the stent receiving area.

13. The stent delivery device of claim 10, wherein the stent is a laser cut stent disposed within the stent receiving area.

14. The stent delivery device of claim 10, wherein the soft durometer polymer has a Shore D hardness value ranging from about 10 to about 80.

15. The stent delivery device of claim 10, wherein the soft durometer polymer includes at least one of a polyolefin, a vinyl, a silicone and a fluoropolymer.

16. The stent delivery device of claim 10, wherein the stent receiving area includes a polymeric layer formed of the soft durometer polymer, wherein the polymeric layer includes a plurality of fingers extending radially outward from the polymeric layer, wherein the plurality of fingers are present in the absence of the stent.

17. The stent delivery device of claim 16, wherein the plurality of fingers are axially spaced along the stent receiving area.

18. The stent delivery device of claim 10, wherein the stent is a low durometer stent that has a column strength less than 17.8 N (4 lbf) in its constrained configuration.

19. A stent delivery device for deploying a low column strength stent, the stent delivery device comprising:
an inner member including a distal region;
a stent receiving area defined within the distal region of the inner member;
a low column strength stent formed of a plurality of stent components disposed on the stent receiving area and convertible between a compressed configuration and an expanded configuration, wherein the low column strength stent has a wall thickness measured from a radially inner surface of a single stent component to a radially outer surface of the single stent component;
the stent receiving area including a soft durometer polymer configured to permit the low column strength stent to sink into the soft durometer polymer and become embedded into the soft durometer polymer to a level of at least one-half or greater than one-half of the wall thickness of the low column strength stent when the low column strength stent is in the compressed configuration; and
an outer member movable between an extended position in which the outer member extends over the low column strength stent and maintains the low column strength stent in the compressed configuration and a retracted position in which the outer member is proximal of the low column strength stent, permitting the low column strength stent to expand into the expanded configuration;
wherein the stent receiving area includes a polymeric layer formed of the soft durometer polymer, wherein the polymeric layer includes a plurality of fingers extending radially outward from the polymeric layer, wherein the plurality of fingers are present in the absence of the stent.

20. The stent delivery device of claim 19, wherein the plurality of fingers are axially spaced along the stent receiving area.

* * * * *